(12) United States Patent
Imai

(10) Patent No.: US 10,142,523 B2
(45) Date of Patent: Nov. 27, 2018

(54) ENDOSCOPE AND CYLINDRICAL STRUCTURE FOR ENDOSCOPE

(71) Applicant: OLYMPUS CORPORATION, Hachioji-shi, Tokyo (JP)

(72) Inventor: Shunichi Imai, Okaya (JP)

(73) Assignee: OLYMPUS CORPORATION, Tokyo (JP)

( * ) Notice: Subject to any disclaimer, the term of this patent is extended or adjusted under 35 U.S.C. 154(b) by 20 days.

(21) Appl. No.: 15/256,161

(22) Filed: Sep. 2, 2016

(65) Prior Publication Data

US 2016/0373624 A1   Dec. 22, 2016

Related U.S. Application Data

(63) Continuation of application No. PCT/JP2015/072083, filed on Aug. 4, 2015.

(30) Foreign Application Priority Data

Aug. 7, 2014 (JP) ................... 2014-161736

(51) Int. Cl.
*A61B 1/12* (2006.01)
*H04N 5/225* (2006.01)
(Continued)

(52) U.S. Cl.
CPC ............. *H04N 5/2252* (2013.01); *A61B 1/00* (2013.01); *A61B 1/0008* (2013.01);
(Continued)

(58) Field of Classification Search
CPC .......... A61B 1/12; A61B 1/121; A61B 1/122; A61B 1/123; A61B 1/125; A61B 1/126;
(Continued)

(56) References Cited

U.S. PATENT DOCUMENTS

2013/0131453 A1* 5/2013 Imai ................... A61B 1/00091
600/156

FOREIGN PATENT DOCUMENTS

JP          H08-47476 A      2/1996
JP          H10-99260 A      4/1998
(Continued)

OTHER PUBLICATIONS

Feb. 16, 2017 International Preliminary Report on Patentability issued in International Patent Application No. PCT/JP2015/072083.
(Continued)

*Primary Examiner* — John P Leubecker
*Assistant Examiner* — Pamela F Wu
(74) *Attorney, Agent, or Firm* — Oliff PLC

(57) ABSTRACT

An endoscope includes a cylindrical member, a first outward flange including a first cutout, a projection projecting inward from an internal circumferential surface of a hole formed in a distal end portion of an insertion section of the endoscope, and capable of being engaged with the first cutout, an elastic member to urge the cylindrical member toward a bottom portion of the hole, and a projecting portion formed to project from the internal circumferential surface of the hole and including a surface facing the bottom portion of the hole.

12 Claims, 14 Drawing Sheets

(51) Int. Cl.
  *A61B 1/00* (2006.01)
  *A61B 1/005* (2006.01)
  *A61B 1/015* (2006.01)
  *A61B 1/018* (2006.01)
  *A61B 1/05* (2006.01)
  *G02B 23/24* (2006.01)
(52) U.S. Cl.
  CPC ........ *A61B 1/0057* (2013.01); *A61B 1/00091* (2013.01); *A61B 1/015* (2013.01); *A61B 1/018* (2013.01); *A61B 1/05* (2013.01); *A61B 1/12* (2013.01); *G02B 23/2476* (2013.01); *H04N 5/2254* (2013.01); *H04N 2005/2255* (2013.01)
(58) Field of Classification Search
  CPC ..... A61B 1/127; A61B 1/128; A61B 1/00112; A61B 1/00119; A61B 1/00064; A61B 1/00091; A61B 1/00094; A61B 1/015
  USPC .................................................. 600/156–159
  See application file for complete search history.

(56) References Cited

FOREIGN PATENT DOCUMENTS

| JP | 2010-119569 A | 6/2010 |
|----|---------------|--------|
| JP | 2013-220253 A | 10/2013 |
| JP | 5323268 B2 | 10/2013 |

OTHER PUBLICATIONS

Oct. 6, 2015 International Search Report issued in International Patent Application No. PCT/JP2015/072083.

\* cited by examiner

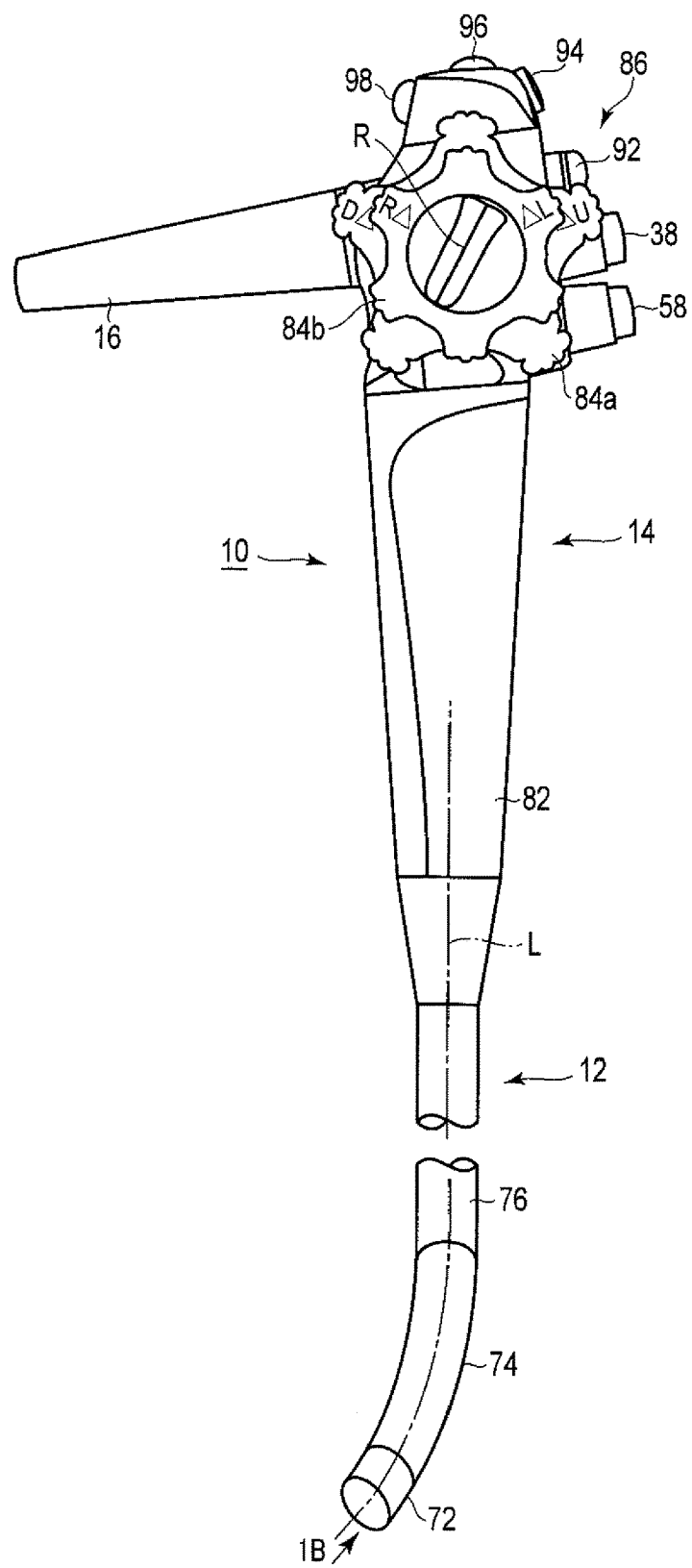
F I G. 1A

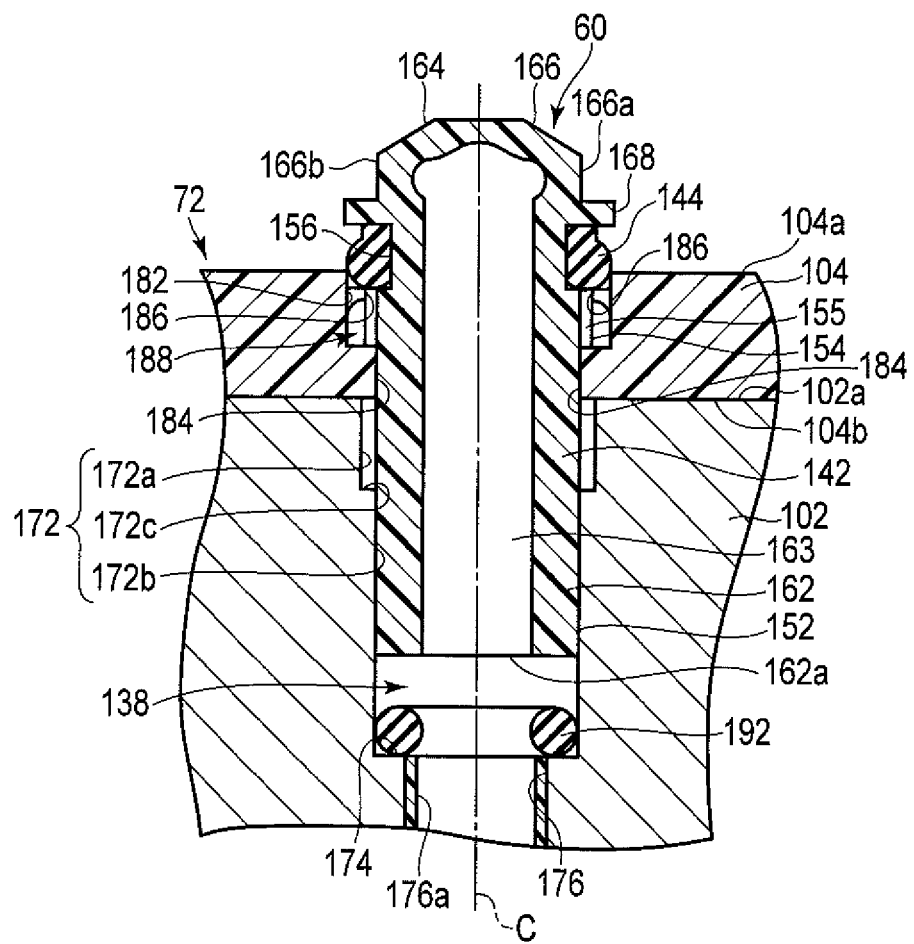
F I G. 6A

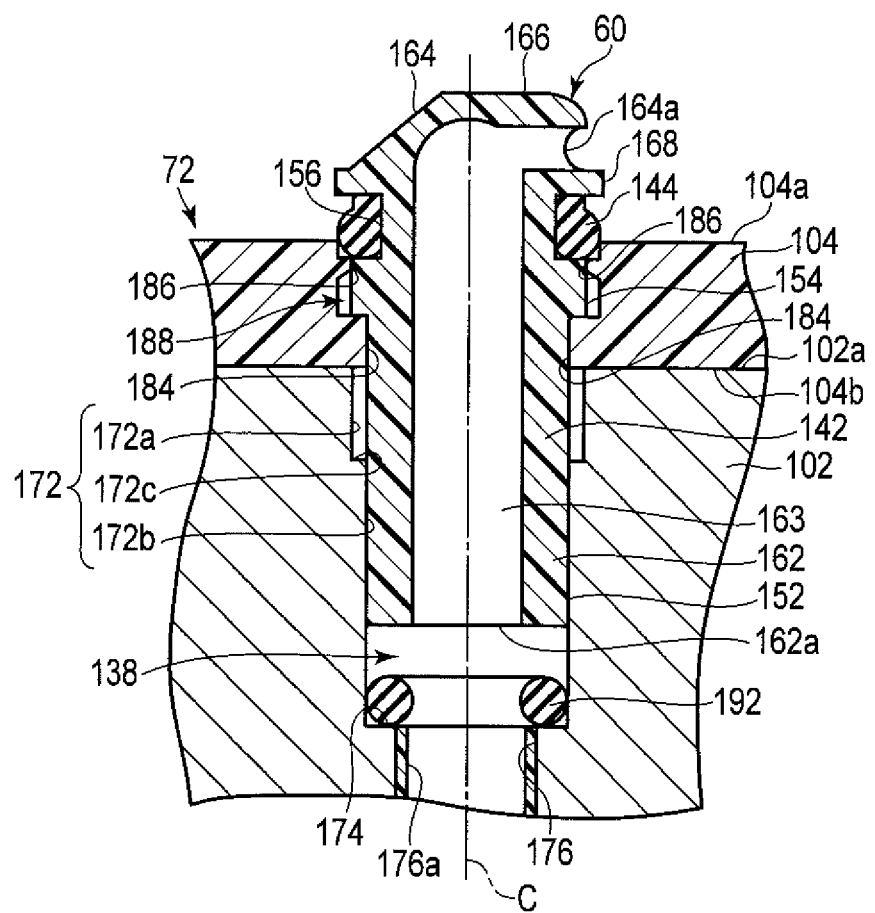
F I G. 6B

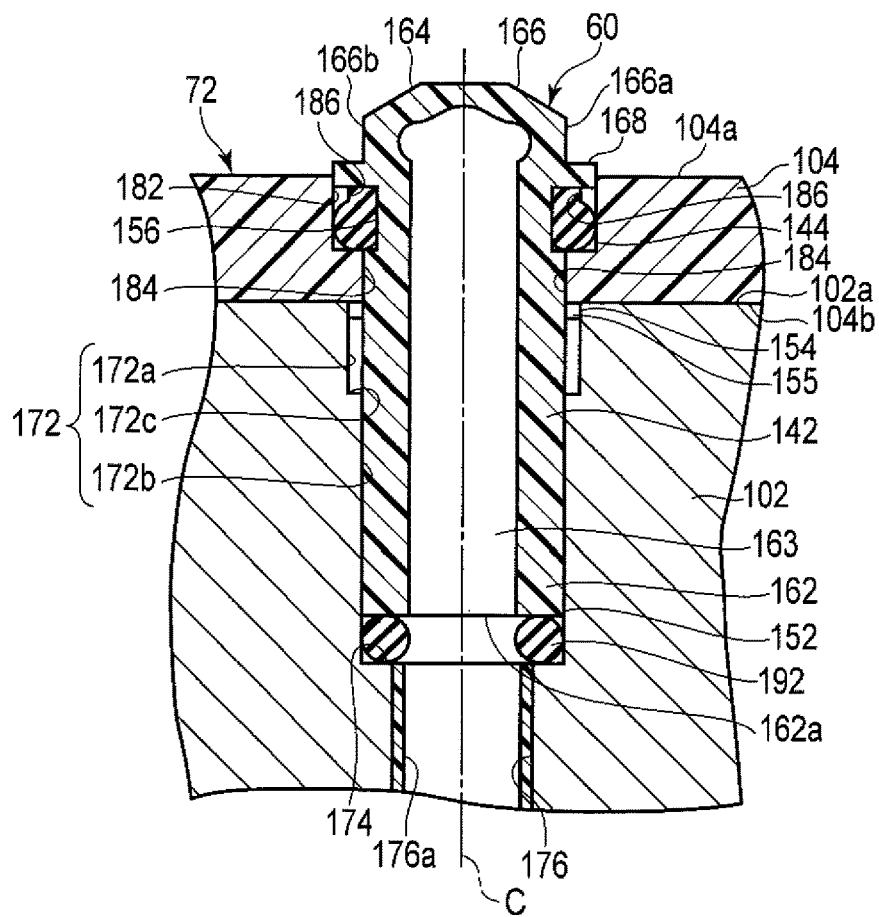
F I G. 7
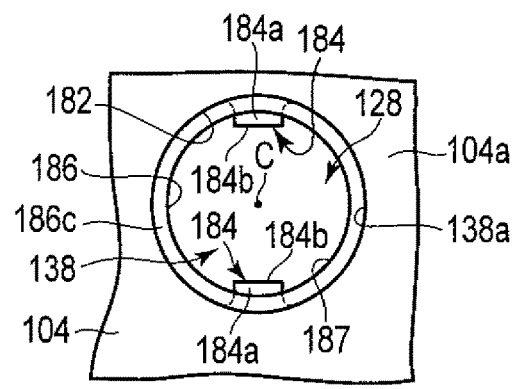
F I G. 8

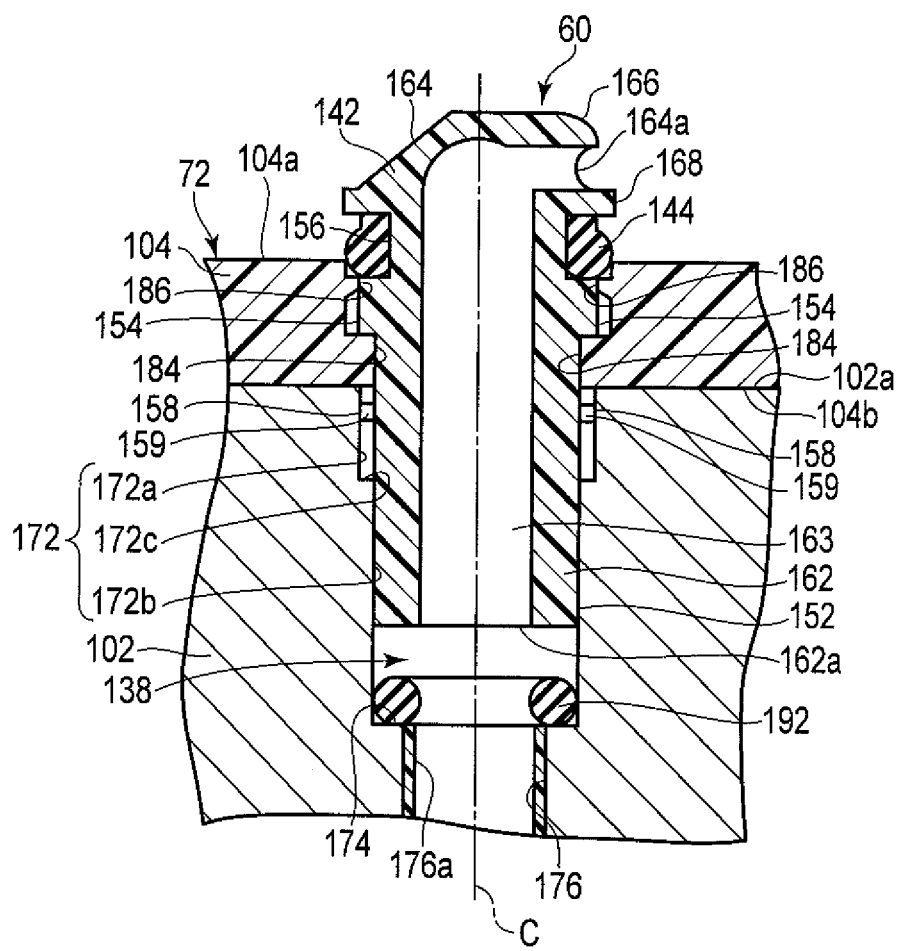
F I G. 12

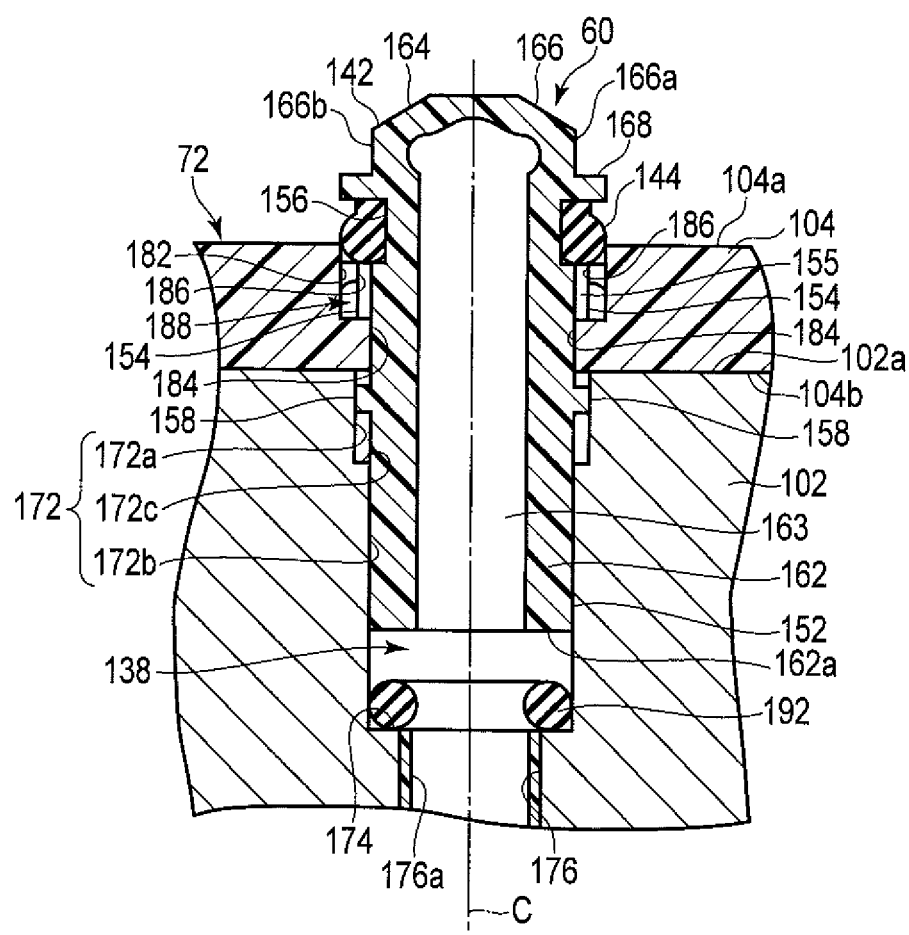
F I G. 13

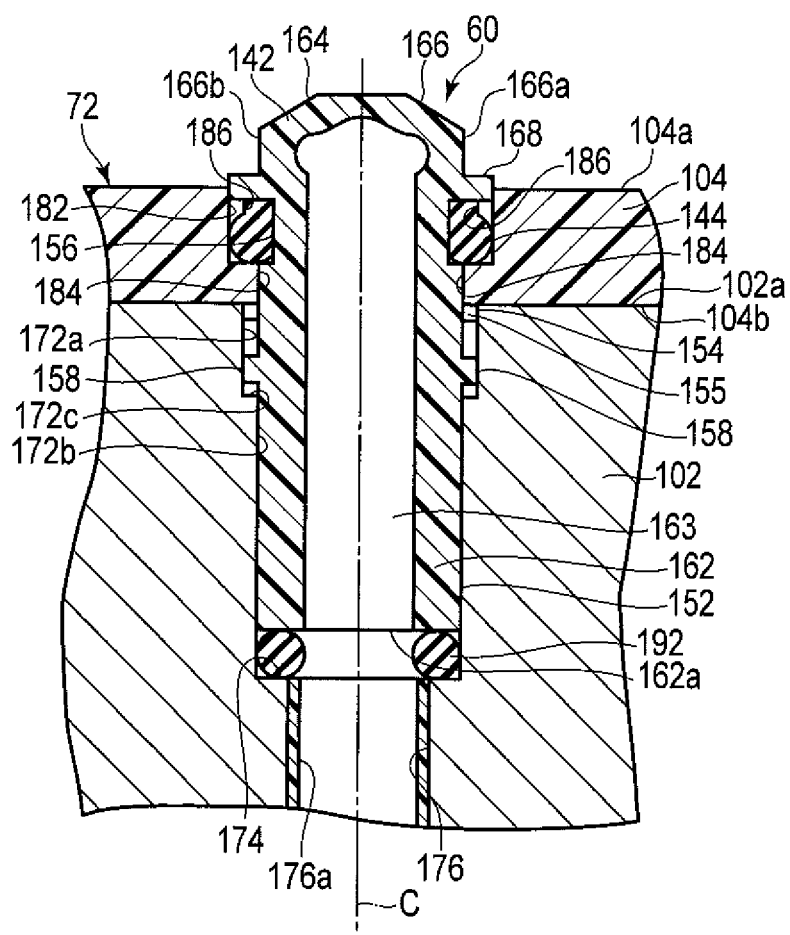
F I G. 14

ENDOSCOPE AND CYLINDRICAL STRUCTURE FOR ENDOSCOPE

CROSS-REFERENCE TO RELATED APPLICATIONS

This application is a Continuation Application of PCT Application No. PCT/JP2015/072083, filed Aug. 4, 2015 and based upon and claiming the benefit of priority from prior Japanese Patent Application No. 2014-161736, filed Aug. 7, 2014, the entire contents of all of which are incorporated herein by reference.

BACKGROUND OF THE INVENTION

1. Field of the Invention

The present invention relates to an endoscope including an insertion section inserted into a narrow hole, and a cylindrical structure for an endoscope disposed at a distal end of the insertion section.

2. Description of the Related Art

For example, Japanese Patent No. 5323268 discloses a structure in which a cylindrical structure such as a nozzle that discharges fluid is rotated around a central axis thereof, and thereby attached to a distal end portion of an insertion section of an endoscope.

BRIEF SUMMARY OF THE INVENTION

According to one aspect of the present invention, an endoscope includes: a cylindrical member inserted into a hole formed in a distal end portion of an insertion section from an opening of the hole toward a bottom portion of the hole, and disposed in the hole; a projecting portion projecting inward in a radial direction from an internal circumferential surface of the hole; an elastic member provided on an external circumferential surface of the cylindrical member, elastically deformed when moved together with the cylindrical member from the opening toward the bottom portion, to get over the projecting portion, the elastic member abutting against a surface of the projecting portion facing the bottom portion of the hole, and elastically deformed to urge the cylindrical member toward the bottom portion; and a regulating portion provided on the external circumferential surface of the cylindrical member and on a side closer to the opening than the elastic member is, and regulating movement toward a side close to the bottom portion in the cylindrical member in a state in which the cylindrical member is disposed in the hole.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic diagram illustrating an endoscope according to first and second embodiments;

FIG. 6A is a schematic vertical cross-sectional view illustrating a state where a straight duct of the nozzle unit is inserted into the hole portion of the distal end hard portion of the insertion section in the endoscope according to the first, embodiment;

FIG. 6B is a schematic vertical cross-sectional view illustrating a state where the vertical cross-sectional view illustrated in FIG. 6A is rotated by 90° with respect to the central axis of the hole portion;

FIG. 7 is a schematic vertical cross-sectional view illustrating a state where the straight duct of the nozzle unit is inserted into the hole portion of the distal end hard portion of the insertion section, and the nozzle unit is attached to the distal end hard portion in the endoscope according to the first embodiment;

FIG. 8 is a schematic top view illustrating the hole portion formed in the distal end hard portion of the insertion section in the endoscope according to a modification of the first embodiment;

FIG. 12 is a schematic vertical cross-sectional view illustrating a state where the nozzle unit illustrated in FIG. 11 is properly rotated with respect to the central axis thereof, and the straight duct is pushed into the depth side of the hole portion by causing projections to pass through second notch portions of a second outward flange;

FIG. 13 is a schematic vertical cross-sectional view illustrating a state where the nozzle unit illustrated in FIG. 12 is rotated by 90° with respect to the central axis thereof, and a fluid discharging port (distal end opening) is turned toward an observation window;

FIG. 14 is a schematic vertical cross-sectional view illustrating a state where a straight duct of the nozzle unit illustrated in FIG. 13 is pushed into the depth side of the hole portion by causing the projections to pass through first notch portions of a first outward flange, and the nozzle unit is fitted into the hole portion.

DETAILED DESCRIPTION OF THE INVENTION

The following is explanation of embodiments to carry out the present invention with reference to drawings.

A first embodiment will be explained hereinafter with reference to FIG. 1A to FIG. 7.

Figure 1B:
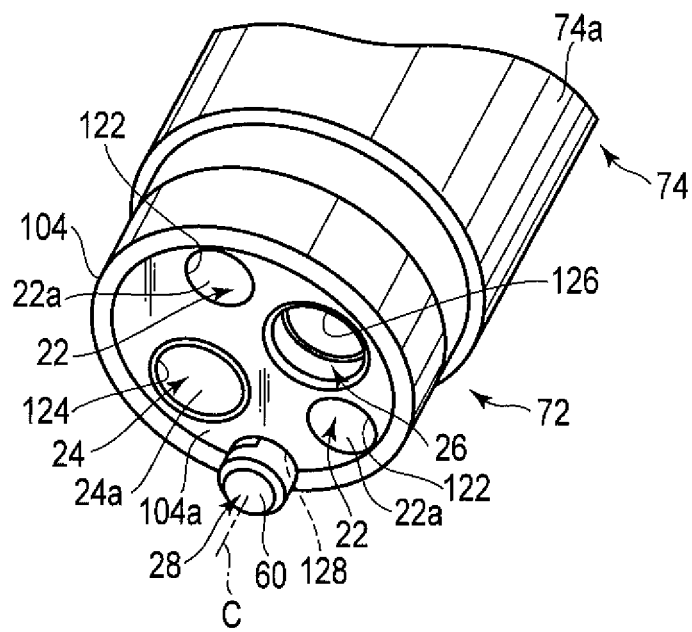
FIG. 1B is a schematic perspective view illustrating a distal end portion and therearound of an insertion section of the endoscope as viewed from a direction of an arrow 1B in FIG. 1A.
Figure 2:
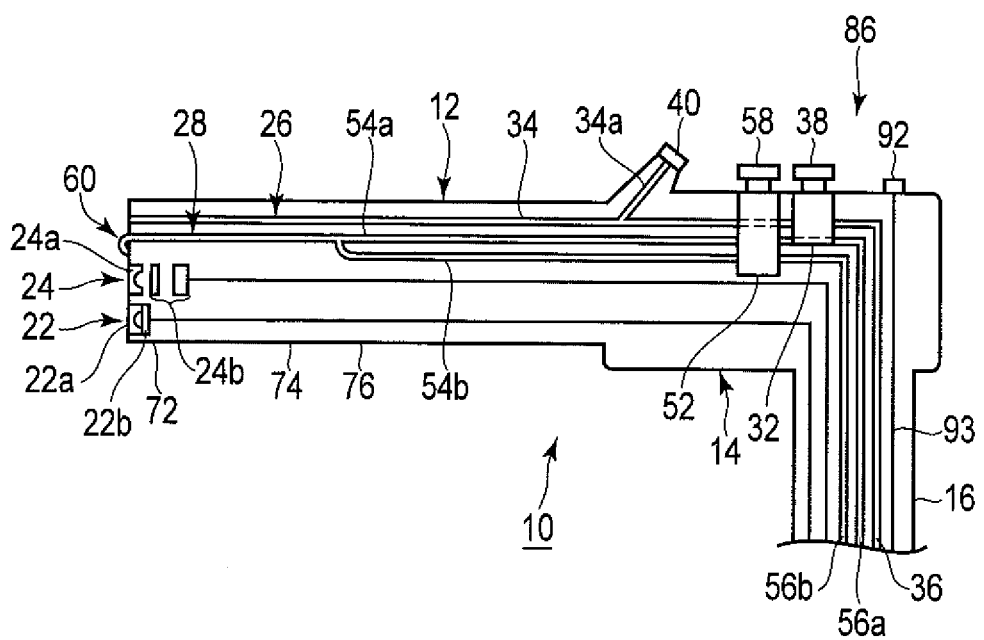
FIG. 2 is a schematic diagram illustrating an illumination optical system, an observation optical system, and various pipelines running through the inside of the endoscope according to the first and second embodiments.

As illustrated in FIG. 1A and FIG. 2, an endoscope 10 includes an insertion section 12 that is inserted into a hole, and an operation section 14 that is held by a user's hand and used for properly operating the endoscope 10 including the insertion section 12. The operation section 14 is disposed at a proximal end portion of the insertion section 12. The insertion section 12 and the operation section 14 are located on a common longitudinal axis L. The operation section 14 includes a universal code 16 that is connected to a control unit (not illustrated) that controls the endoscope 10.

As illustrated in FIG. 1B and FIG. 2, the endoscope 10 includes therein publicly-known illumination optical systems 22, each of which illuminates the inside of the hole, and a publicly-known observation optical system 24 that images the inside of the hole illuminated by the illumination optical system 22 to observe the inside of the hole.

Each of the illumination optical systems 22 has a structure in which a light emitting member 22b such as a light guide fiber and a LED is disposed on the rear end side of an illumination window 22a, and illumination light is emitted through the illumination window 22a, to illuminate the subject. The observation optical system 24 has a structure in which an imaging unit 24b, for example, is disposed on the rear end side of an observation window 24a, and a subject image illuminated with the illumination light is imaged through the observation window 24a.

The observation window 24a preferably has an equal distance from each of the illumination windows 22a.

In the present embodiment, the endoscope 10 further includes a suction unit 26 that sucks a living tissue and blood and the like, and an air/water feed unit (air/liquid feed unit) 28 that feeds air or liquid to wash the observation window 24a of the observation optical system 24 or remove substances attached to the observation window 24a.

The suction unit 26 includes a first cylinder 32, suction pipelines 34 and 36 coupled with the first cylinder 32, and a first button unit (pressure valve unit) 38 serving as a pressing unit that is pressed along the longitudinal axis of the first cylinder 32. The first button unit 38 exhibits a suction function in a pressed state.

The first button unit (pressing unit) 38 is connected with the suction pipelines 34 and 36 that are disposed inside a holding portion 82 described later. The suction pipeline 34 includes a branched pipeline 34a that is branched therefrom.

An end portion of the branched pipeline 34a is connected to a treatment tool inlet (forceps port) 40. With the structure, the suction pipeline 34 and the branched pipeline 34a forms a channel through which a treatment tool (not illustrated) is inserted.

The structure of the first cylinder 32, the coupling state of the suction pipelines 34 and 36 with the first cylinder 32, and the structure of the first button unit 38 itself are publicly known, and detailed explanations thereof are omitted herein.

The air/water feed unit 28 includes a second cylinder 52, fluid pipelines 54a, 54b, 56a, and 56b coupled with the second cylinder 52, and a second button unit (pressure valve unit) 58 serving as a pressing unit that is pressed along the longitudinal axis of the second cylinder 52. The second button unit 58 exhibits an air feed function and a liquid feed function by properly performing an operation of covering a communicating hole (not illustrated) and a pressing operation.

The second button unit (pressing unit) 58 is connected with the fluid pipelines 54a, 54b, 56a, and 56b that are disposed inside the holding portion 82 described later. The structure of the second cylinder 52, the coupling state of the fluid pipelines 54a, 54b, 56a, and 56b with the second cylinder 52, and the structure of the first button unit 58 itself are publicly known, and detailed explanations thereof are omitted herein.

An endoscope nozzle unit (cylindrical structure for endoscope) 60 is disposed at a distal end of the fluid pipeline 54a. The nozzle unit 60 is capable of discharging air from a fluid discharge port 164a described later through the fluid pipeline (air feed pipeline) 56a and the fluid pipeline (air feed pipeline) 54a, by a proper operation of the second button unit (pressure valve unit) 58 disposed on the second cylinder 52. The nozzle unit 60 is also capable of discharging liquid, such as a physiological salt solution, from the fluid discharge port 164a described later through the fluid pipeline (liquid feed pipeline) 56b, the fluid pipeline (liquid feed pipeline) 54b, and the fluid pipeline (air/fluid feed pipeline) 54a, by a proper operation of the second button unit (pressure valve unit) 58 disposed on the second cylinder 52.

As illustrated in FIG. 1A and FIG. 2, the insertion section 12 includes a distal end hard portion (distal end portion) 72, a bending portion 74, and a flexible tube-shaped member 76 in this order from the distal end toward the proximal end, along the longitudinal axis L.

The distal end hard portion 72 is disposed at the distal end of the insertion section 12 that is inserted into a narrow hole such as a body cavity, and formed as a distal end portion. The tube-shaped member 76 is preferably a flexible member such as a flexible tube of an insertion section of a flexible endoscope, but may be, for example, a hard tube having no flexibility and formed of a metal material such as a stainless alloy material.

The bending portion 74 includes a bending tube in which a plurality of publicly-known bending pieces are arranged along the axial direction of the insertion section 12, and adjacent bending pieces are relatively rotatable with respect to each other. A distal end of a wire is fixed to the bending piece located on the most distal end side, and the wire is successively inserted through the bending pieces to the bending piece adjacent to the proximal end side. The proximal end of the wire extends through the tube-shaped member 76 to, for example, the operation section 14. When the operator operates knobs 84a and 84b of the operation section 14 to move the wire in the axial direction thereof, the operator can properly bend the bending portion 74. With the structure, by bending the bending portion 74, a distal end surface 104a of the distal end hard portion 72 can be directed to a desired direction. The external layer of the bending portion 74 is covered with an outer tube 74a (see FIG. 1B).

As illustrated in FIG. 1A, the operation section 14 includes a cylindrical holding portion 82 with the longitudinal axis L defined by the insertion section 12 connected thereto, the first and second knobs 84a and 84b provided outside the holding portion 82 and serving as a bending operation input unit in which an input operation to bend the bending portion 74 of the insertion section 12 is performed and having an input axis R, and a switching portion 86 to perform various switching.

The first knob 84a is used for bending the bending portion 74 in a U direction and a D direction by a publicly-known mechanism. The second knob 84b is used for bending the bending portion 74 in an R direction and an L direction by a publicly-known mechanism.

The switching portion 86 includes the first and second button units 38 and 58 serving as the pressing units described above, and a plurality of, first to fourth switches 92, 94, 96, and 98 herein provided outside the holding portion 82. The first to fourth switches 92, 94, 96, and 98 are pressed to switch the function.

As illustrated in FIG. 2, a proper function is set on the first switch 92 by a controller (not illustrated) that is electrically connected thereto through a signal line 93 inserted through the inside of the universal code 16, and the first switch 92 exhibits the proper function when being pressed. Although not illustrated, the second to fourth switches 94, 96, and 98 are also electrically connected to the controller (not illustrated) through respective signal lines inserted through the inside of the universal code 16, in the same manner as the signal line 93 for the first switch 92. With the structure, respective proper functions are set on the second to fourth switches 94, 96, and 98, and the second to fourth switches 94, 96, and 98 exhibit the respective proper functions when being pressed.

The distal end hard portion (distal end portion) 72 includes a distal end portion main body (base member) 102, and a distal end cover 104 attached to a distal end side of the distal end portion main body 102 and covering the external circumferential surface of the distal end portion main body 102. The distal end cover 104 forms the distal end surface 104a of the insertion section 12. The respective distal ends of the illumination optical systems 22, the observation optical system 24, and the suction unit 26 are fixed to the distal end portion main body 102. A rear surface 104b of the distal end cover 104 is fixed to a distal end 102a of the distal end portion main body 102 by adhesion or the like. In the present embodiment, after the distal end cover 104 is fixed to the distal end portion main body 102, nozzle unit 60 described later and forming the distal end of the air/water feed unit 28 is attached thereto.

The distal end portion main body 102 is formed in a substantially cylindrical shape and formed of a metal material such as a stainless steel material, or a hard resin material. The distal end cover 104 protects the distal end side of the distal end portion main body 102, and formed in a substantially cylindrical shape and formed of a resin material having heat resistance, insulating property, acid resistance, and resistance to bases, such as a polysulfone resin. Because the distal end cover 104 is formed of a resin material, projections 184 and an inward flange (projecting portions) 186 described later can be manufactured relatively easily, in comparison with the case of processing a metal material.

The distal end portion main body 102 is provided with illumination optical system through holes (not illustrated) in which the illumination optical systems 22 are disposed, an observation optical system through hole (not illustrated) in which the observation optical system 24 is disposed, a channel through hole (not illustrated), and an air/water feed through hole (first hole portion) 118 in which the nozzle unit 60 is disposed. The through holes of the distal end portion main body 102 extend along axes parallel with the longitudinal axis L of the insertion section 12.

The distal end cover 104 is provided with illumination optical system through holes 122 in which the respective illumination windows 22a of the illumination optical systems 22 are disposed, an observation optical system through hole 124 in which the observation window 24a of the observation optical system 24 is disposed, a channel through hole 126 in which an opening of the suction unit 26 is formed, and an air/water feed through hole (second hole portion) 128 in which the nozzle unit 60 is disposed. The through holes 122, 124, 126, and 128 of the distal end cover 104 extend along axes parallel with the longitudinal axis L of the insertion section 12.

The illumination optical system through holes 122 of the distal end cover 104 communicate with the respective illumination optical system through holes (not illustrated) of the distal end portion main body 102. The communicating through holes form hole portions in which the illumination windows 22a and the light emitting members 22b of the illumination optical systems 22 are disposed. The observation optical system through hole 124 of the distal end cover 104 communicates with the observation optical system through hole (not illustrated) of the distal end portion main body 102. The communicating through holes form a hole portion in which the observation window 24a and the imaging unit 24b of the observation optical systems 24 are disposed. The channel through hole 126 of the distal end cover 104 communicates with the channel through hole (not illustrated) of the distal end portion main body 102. The communicating through holes form a hole portion that causes the treatment tool to project from the distal end surface 104a of the distal end cover 104 through the suction pipeline 34. The air/water feed through hole 128 of the distal end cover 104 communicates with the air/water feed through hole 118 of the distal end portion main body 102. The through holes 118 and 128 communicating with each other form a hole portion 138 in which the nozzle unit 60 is disposed. Specifically, the hole portion 138 is formed in a recessed shape from the distal end surface 104a of the distal end cover 104 toward the proximal end side along the longitudinal axis L of the insertion section 12. The hole portion 138 includes cylindrical internal circumferential surfaces 172 and 182 that define a central axis C of the hole portion 138, and an annular bottom portion 174 formed on the proximal end side of the internal circumferential surface 172. The hole portion 138 forms part of a flow channel through which the fluid in the fluid pipeline 54a passes.

Figure 3:
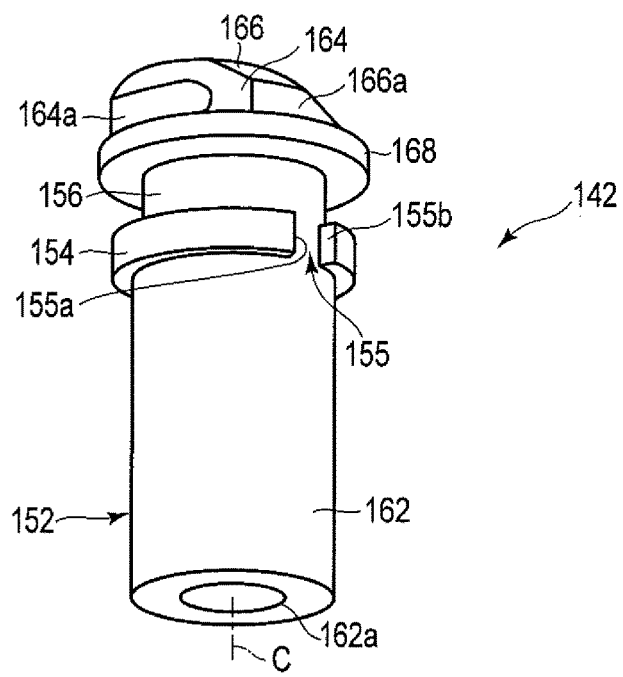
FIG. 3 is a schematic perspective view illustrating a nozzle (cylindrical member) attached to the distal end portion of the insertion section of the endoscope according to the first embodiment.
Figure 4:
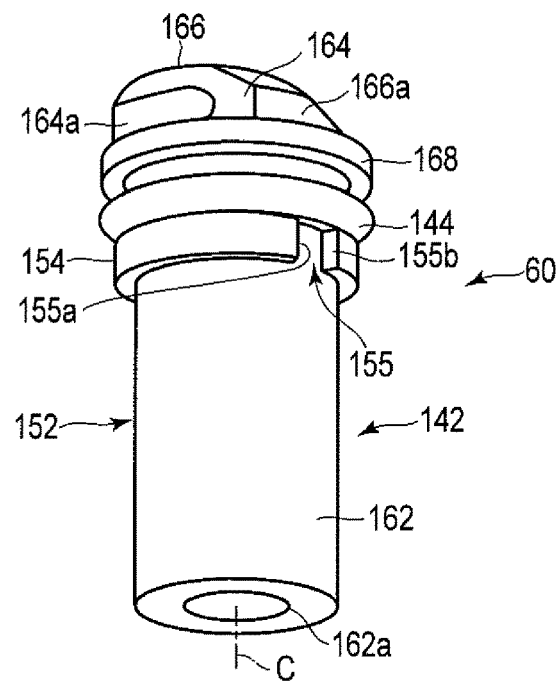
FIG. 4 is a schematic perspective view illustrating a nozzle unit (cylindrical structure) attached to the distal end portion of the insertion section of the endoscope according to the first embodiment.

As illustrated in FIG. 3 and FIG. 4, the nozzle unit 60 includes a nozzle (cylindrical member) 142, and an annular gasket (first elastic member) 144 that is elastically deformable. The nozzle 142 includes a nozzle main body (cylindrical body) 152, an outward flange (first outward flange) 154, and an annular recessed portion 156 in which the gasket 144 is disposed. The gasket 144 may suitably be a simple O ring, as well as the shape illustrated in FIG. 4. The gasket (first elastic member) 144 is formed to be hard to deform more than an elastically deformable O ring (annular second elastic member) 192 described later.

The annular recessed portion 156 in which the gasket 144 is disposed serves as an external circumferential surface of a straight duct 162 described later, and is formed between the outward flange 154 and an annular edge portion (regulating portion) 168. Specifically, the gasket (first elastic member) 144 is disposed on the external circumferential surface of the straight pipe 162 of the nozzle main body 152, and between the outward flange 154 and the fluid discharge port (distal end opening) 164a. In other words, the gasket 144 is provided on the external circumferential surface of the nozzle 142 and on the more distal end side than the outward flange 154. The gasket 144 gets over an inward flange 186 described later from the side close to the distal end surface 104a toward the annular bottom portion 174, and is supported between the projections 184 and the inward flange 186, to be disposed in a receiving space 188 and fit the nozzle 142 into the hole portion 138.

The nozzle main body 152 includes the straight duct 162, and a curved duct 164. The straight duct 162 is received in the through hole 118 of the distal end portion main body 102 and the through hole 128 of the distal end cover 104, that is, the hole portion 138. The straight duct 162 includes an annular edge portion 162a that is received in the hole portion 138 and forms, at the proximal end thereof, a proximal end opening communicating with the fluid pipeline 54a. The curved duct 164 includes the fluid discharge port (distal end opening) 164a in a position where at least part of which projects from the distal end surface 104a of the distal end cover 104 to the distal end side along the central axis C. The observation window 24a of the distal end of the observation optical system 24 is disposed in the distal end surface 104a of the distal end cover 104, and the fluid discharge port (distal end opening) 164a is directed to the observation window 24a in the state where the nozzle 142 (nozzle unit 60) is attached to the distal end hard portion 72 of the insertion section 12. The nozzle main body 152 forms a fluid passage 163, that is, a flow channel, between the annular edge portion (proximal end opening) 162a and the fluid discharge port (distal end opening) 164a. This structure enables the nozzle 142 to supply the fluid from the passage 163 to the observation window 24a.

As illustrated in FIG. 3, FIG. 4, and FIG. 6A to FIG. 7, the curved pipe 164 forms the fluid discharge port 164a, and forms a nozzle head 166 to be engaged with the jig. The nozzle head 166 includes a pair of flat surface portions 166a and 166b. The flat surface portions 166a and 166b are held by the jig, and thereby the nozzle unit 60 is easily positioned in the circumferential direction with respect to the central axis C for the hole portion 138.

The annular edge portion 168 is formed on the external circumference around the boundary between straight duct 162 and the curved duct 164. The annular edge portion 168 is flush with, or substantially flush with the distal end surface 104a of the distal end cover 104, in the state where the nozzle unit 60 is fitted into the hole portion 138.

The outward flange 154 is formed on the external circumferential surface of the straight duct 162 of the nozzle main body 152. The outward flange 154 includes cutout portions (cutout grooves) 155, to define the circumferential direction of the nozzle main body 152 with respect to the central axis C for the distal end hard portion 72 of the insertion section 12. The cutout portions 155 let the projections 184 described later pass along the axial direction of the central axis C, to dispose the straight duct 162 of the nozzle main body 152 inside the internal circumferential surface 182 of the hole portion 138. In the present embodiment, the outward flange 154 is formed in an arc shape, not a ring shape. With the structure, the outward flange 154 has a structure in which end portions 155a and 155b are opposed to each other in the circumferential direction of the central axis C.

Figure 5A:
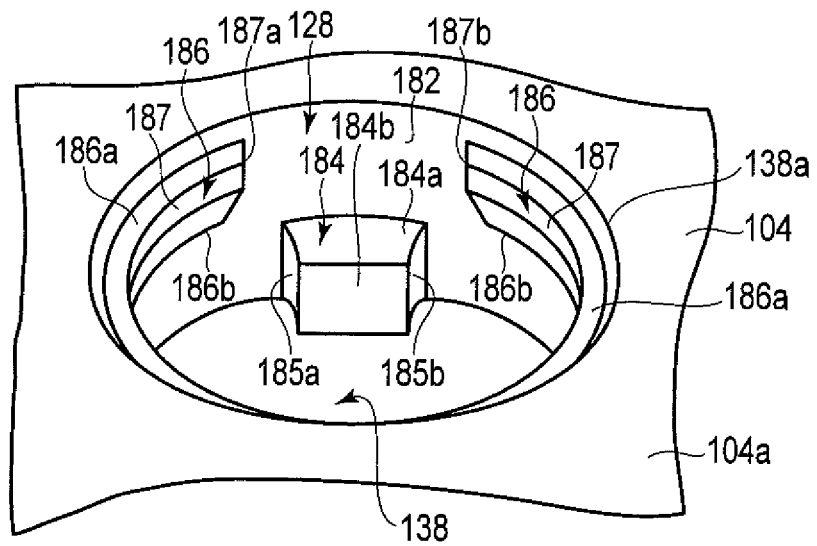
FIG. 5A is a schematic perspective view illustrating a structure of a hole portion formed in a distal end cover of a distal end hard portion of the insertion section in the endoscope according to the first embodiment.
Figure 5B:
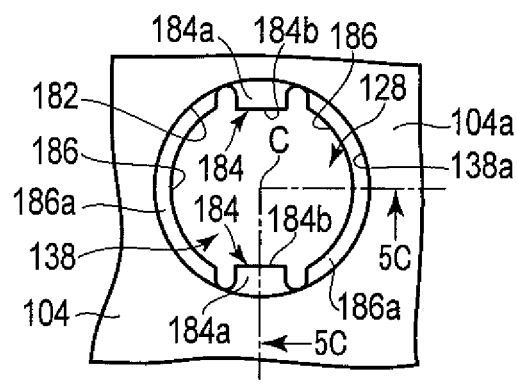
FIG. 5B is a schematic top view illustrating the hole portion formed in the distal end hard portion of the insertion section in the endoscope.
Figure 5C:
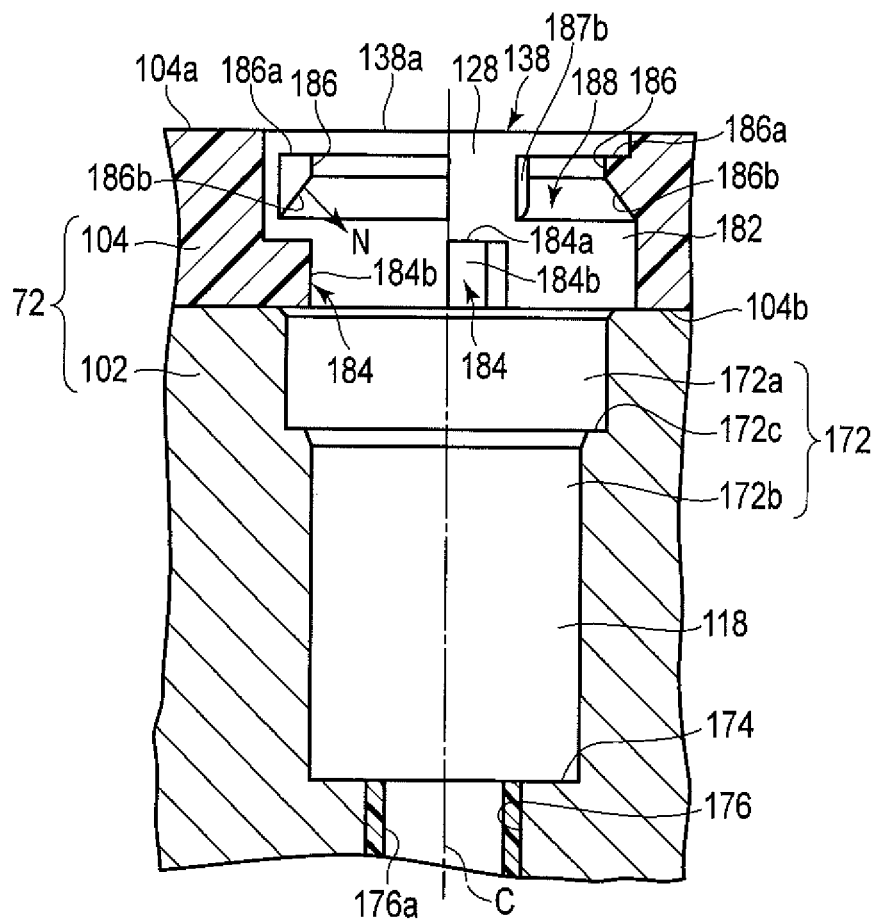
FIG. 5C is a schematic cross-sectional view taken along line 5C-5C of arrows in FIG. 5B.

As illustrated in FIG. 5A to FIG. 5C, the air/water feed through hole 118 of the distal end portion main body 102 includes the cylindrical internal circumferential surface 172 that defines the central axis C thereof, the annular bottom portion 174, and a communicating port 176 in which a connection pipe 176a connected with the distal end of the fluid pipeline 54a is disposed. Specifically, the through hole 118 extends along the central axis C. The connection pipe 176a is preferably formed of a hard material such as a stainless steel material.

The air/water feed through hole 118 of the distal end portion main body 102 forms part of the hole portion 138, and receives the annular edge portion (proximal end opening) 162a of the nozzle main body 152.

The internal circumferential surface 172 is formed to have a large-diameter portion 172a disposed on the side opposed to the rear surface 104b of the distal end cover 104 and having a large diameter, and a small-diameter portion 172b disposed on the side close to the annular bottom portion 174 and having a diameter smaller than the diameter on the side close to the distal end cover 104. A step portion 172c (see FIG. 6A to FIG. 7) is formed between the large-diameter portion 172a and the small-diameter portion 172b. Among the outward flange 154 of the nozzle 142, a portion thereof close to the annular edge portion 162a can be disposed in the large-diameter portion 172a. The annular edge portion 162a of the straight duct 162 of the nozzle 142 is disposed in the small-diameter portion 172b.

As illustrated in FIG. 5A to FIG. 5C, the air/water feed through hole 128 of the distal end cover 104 includes the cylindrical internal circumferential surface 182 that defines the central axis C thereof, the projections 184 that project from the internal circumferential surface 182 inward in the radial direction, and the inward flange (step portion) 186 that projects from the internal circumferential surface 182 inward in the radial direction. Specifically, the air/water feed through hole 128 of the distal end cover (cover member) 104 forms part of the hole portion 138, is provided with the distal end surface 104a, the projections 184, and the inward flange 186, covers the distal end portion main body 102, and forms the distal end surface 104a.

The projections 184 are engaged with the respective cutout portions (cutout grooves) 155 of the outward flange (first outward flange) 154, to position the nozzle 142 with respect to the circumferential direction of the internal circumferential surface 182 of the hole portion 138. Specifically, the cutout portions 155 can be engaged with the projections 184, and the nozzle 142 is positioned in the circumferential direction with respect to the central axis C with the projections 184.

The internal circumferential surface 182 of the distal end cover 104 is formed to be recessed from the distal end surface 104a of the distal end cover 104 toward the proximal end side along the longitudinal axis L of the insertion section 12. The internal diameter of the internal circumferential surface 182 is formed to be slightly larger than the external diameter of the outward flange 154 and the external diameter of the annular edge portion 168 of the nozzle 142.

In the present embodiment, the inward flange 186 is formed in an arc shape projecting from the internal circumferential surface 182 toward the central axis C. The inward flange 186 has an arc-shaped surface 186a disposed at a proper depth from the distal end surface 104a of the distal end cover 104. The annular edge portion 168 of the nozzle 142 can abut against the arc-shaped surface 186a. The arc-shaped surface 186a is preferably parallel with the distal end surface 104a. The arc-shaped surface 186a allows the annular edge portion 168 of the nozzle 142 to abut against it, and prevents the annular edge portion 162a of the nozzle 142 from abutting against the annular bottom portion 174. With this structure, the arc-shaped surface 186a of the inward flange 186 positions the depth of the nozzle unit 60 with respect to the hole portion 138.

The inward flange 186 is shifted in position from the projections 184 along the central axis C, and apart therefrom with a proper distance. The inward flange 186 is formed in a position (distal end side) close to the distal end surface 104a beyond the projections 184 in the internal circumferential surface 182 of the hole portion 138. The inward flange 186 is formed in a state apart from the projections 184 along the central axis C and not interfering with the projections 184.

The inward flange 186 includes end portions 187a and 187b that are opposed to each other along the circumferential direction of the central axis C. Each of the projections 184 is disposed between the adjacent end portions 187a and 187b of the inward flange 186, when the annular bottom portion 174 of the hole portion 138 is viewed from the distal end surface 104a.

In the inward flange 186, an inclined surface 186b inclined with respect to the central axis C is formed in a region opposite to the distal end surface 104a. A normal N of the inclined surface 186b is directed to the large-diameter portion 172a, the small-diameter portion 172b, or the annular bottom portion 174.

The projections 184 are located in a position flush with or adjacent to the rear surface 104b of the distal end cover 104. The projections 184 project from the internal circumferential surface 182 toward the central axis C. The projection amount of the projections 184 allows the projections 184 to be slidable on the external circumferential surface of the straight duct 162 of the nozzle 142, or prevents the projections 184 from contacting the external circumferential surface. The circumferential width of each of the projections 184 is formed to be slightly smaller than the width (distance between the end portions 155a and 155b) of each of the cutout portions 155 formed in the outward flange 154 of the nozzle 142.

The space between an upper surface 184a of the projection 184 and the inward flange 186 serves as a gradient space formed by the inclined surface 186a from the inward flange 186, and includes a receiving space 188 that receives the gasket 144 in the state where the nozzle unit 160 is fitted into the hole portion 138. The inclined surface 186b of the inward flange 186 presses the gasket 144 toward the side (upper surface 184a) close to the projections 184, in the state where the gasket (first elastic member) 144 gets over the inward flange 186. The gasket 144 is elastically deformed when the gasket 144 is moved toward the bottom portion 174 through the opening 138a together with the nozzle main body 152, and gets over the inward flange 186. Thereafter, the gasket 144 abuts against the surface 186b of the inward flange 186 directed to the bottom portion 174 of the through hole 138, and is elastically deformed to urge the nozzle main body 152 toward the bottom portion 174.

In the present embodiment, side surfaces 185a and 185b of each of the projections 184 are disposed between the end portions 187a and 187b of the inward flange 186 (see FIG. 5B), but the end portions 187a and 187b may suitably be disposed above the upper surface 184a of each of the projections 184. In this case, the projecting amount of the projecting surface 184b of each of the projections 184 from the internal circumferential surface 182 toward the central axis C is formed larger than the projecting amount of the projecting surface 187 of the inward flange 186 from the internal circumferential surface 182 toward the central axis C.

In the present embodiment, suppose that two cutout portions 155 are formed in the outward flange 154, and two projections 184 (see FIG. 5B) are formed. Because the projections 184 are formed in opposed positions apart from each other by 180° with respect to the central axis C, the cutout portions 155 are also formed in positions apart from each other by 180°. The cutout portions 15 and the projections 184 are not necessarily formed in positions apart from each other by 180°, but may suitably be formed in positions shifted by the same angle.

The structure may suitably be provided with one cutout portion 155 of the outward flange 154 of the nozzle 142, and one projection 184 of the distal end cover 104.

The depth of the large-diameter portion 172a formed in the cylindrical internal circumferential portion 172 of the air/water feed through hole 118 of the distal end portion main body 102 in the present embodiment is formed deeper than the depth into which part of the outward flange 154 can be inserted, to simplify the explanation in the second embodiment described later. However, it suffices that the large-diameter portion 172 has a depth into which part of the outward flange 154 can be inserted.

The following is explanation of the function in the case where the nozzle unit 60 is fitted into the hole portion 138 of the distal end hard portion (distal end portion of the insertion section 12) 72 in the insertion section 12 according to the present embodiment.

The nozzle unit 60 (see FIG. 4) is formed by mounting the annular gasket 144 on the annular recessed portion 156 of the nozzle 142 illustrated in FIG. 3. The gasket 144 may be disposed in the annular recessed portion 156 from the head portion 166 of the nozzle 142 through the outside of the annular edge portion 168, or may be disposed in the annular recessed portion 156 from the annular edge portion 162a through the outside of the outward flange 154.

The O ring 192 is disposed on the annular bottom portion 174 from the opening 138a of the distal end surface 104a, through the internal circumferential surface 182 of the through hole 128 of the distal end cover 104, and the internal circumferential surface 172 of the through hole 118 of the distal end portion main body (base member) 102. Specifically, the O ring 192 is disposed on the annular bottom portion 174 of the hole portion 138. The external diameter of the O ring 192 is the same as, or slightly smaller than, the internal diameter of the small-diameter portion 172b. The O ring 192 is formed of a material that is softer than the gasket 144.

As illustrated in FIG. 6A and FIG. 6B, the annular edge portion 162a of the nozzle unit 60 is inserted through the opening 138a of the hole portion 138 of the distal end hard portion 72 toward the annular bottom portion 174. Specifically, the nozzle unit 60 is inserted into the hole of the through hole 138 formed in the distal end 104a of the insertion section 12 from the opening 138a of the through hole 138 toward the annular bottom portion 174, and thereby the nozzle main body 152 of the nozzle unit 60 is disposed inside the through hole 138. The cutout portions 155 of the outward flange 154 of the nozzle unit 60 are opposed to the projections 184 formed on the internal circumferential surface 182 of the through hole 128 of the distal end cover 104 in the hole portion 138 of the distal end hard portion 72.

Specifically, the discharge port 164a of the nozzle unit 60 is caused to rightly face the observation window 24a of the observation optical system 24. With the structure, the orientation of the nozzle unit 60 with respect to the distal hard portion 72 of the insertion section 12 is regulated.

In this state, the gasket 144 is placed on the arc-shaped surface 186a on the upper side (position adjacent to the distal end surface 104a) of the inward flange 186. In this state, the annular edge portion 162a of the straight pipe 162 of the nozzle unit 60 is adjacent to the O ring 192 disposed on the annular bottom portion 174 of the hole portion 138. Specifically, when the gasket (first elastic member) 144 is disposed on the distal end surface 104a side above the inward flange 186, the O ring 192 is apart from the annular edge portion (proximal end opening) 162a of the straight duct 162 of the nozzle main body 152.

In this state, the nozzle unit 60 is pushed toward the depth side of the hole portion 138, and the annular edge portion 162a of the nozzle unit 60 is moved toward the O ring 192 disposed on the annular bottom portion 174 of the hole portion 138. As illustrated in FIG. 7, the gasket 144 is elastically deformed, and moved toward the depth side of the hole portion 138 through the inside of the inward flange 186. On the other hand, the annular edge portion 162a of the straight duct 162 of the nozzle main body 152 pushes the O ring 192 against the annular bottom portion 174. Specifically, when the gasket (first elastic member) 144 becomes close over the inward flange 186, the O ring 192 supports the annular edge portion (proximal end opening) 162a. With the structure, when the nozzle 142 is disposed in the hole portion 138, the gasket (first elastic member) 144 abuts against the proximal end side of the inward flange 186 and is elastically deformed, to urge the nozzle 142 toward the proximal end of the hole portion 138. In addition, when the nozzle 142 is disposed in the hole portion 138, the O ring 192 abuts against the annular bottom portion 174 and is elastically deformed, to urge the proximal end of the nozzle 142 toward the distal end of the hole portion 138.

In this state, each of the projections 184 is disposed in the corresponding cutout portion 155 between the end portions 155a and 155b formed in the outward flange 154. With the structure, the nozzle 142 is positioned in the rotational direction with respect to the hole portion 138, in the state where the projections 184 of the distal end cover 184 enter and are engaged with the cutout portions 155 of the outward flange 154 of the nozzle 142. The outward flange 154 may be disposed inside the internal circumferential surface 182 of the through hole 128 of the distal end cover 104, or may be disposed inside the large-diameter portion 172a of the through hole 118 of the distal end portion main body 102 as well as inside the internal circumferential surface 182 of the through hole 128 of the distal end cover 104. FIG. 7 illustrates the latter state.

Because the inward flange 186 includes the inclined surface 186b, the inward flange 186 presses the gasket 144 toward the depth side of the hole portion 138. Accordingly, the inward flange 186 fixes the nozzle 142. The gasket 144 is formed of a material harder than the O ring 192.

The annular edge portion 162a compresses the O ring 192 to secure water-tightness between the end surface of the connection pipe 176a and the nozzle 142, and causes force to push back the nozzle 142. The gasket 144 enters the receiving space 188 beyond the inward flange 186 of the hole portion 138, and is compressed with the inclined surface 186b to secure water-tightness from the distal end surface 104a side, and causes force to push the annular edge portion 162a of the nozzle 142 into the O ring 192. The gasket 144 is harder than the O ring 192, and the gasket 144 has stronger force than that of the O ring 192. For this reason, the elastic force of the gasket 144 to press the O ring 192 against the annular bottom portion 174 with the annular edge portion 162a and maintain the state of being in contact with the inclined surface 186b of the inward flange 186 is stronger than the elastic force of the O ring 192 to move the gasket 194 to the outside of the hole portion 138 through the inside of the inward flange 186. This structure prevents the nozzle unit 60 from falling out of the hole portion 138.

The annular edge portion 168 is provided on the opening 138a side above the gasket 144 on the external circumferential surface of the nozzle main body 152, and controls movement toward the bottom portion 174 side in the nozzle main body 152 in the state where the nozzle main body 152 is disposed in the through hole 138.

In this state, the O ring 192 is in close contact with the end portion of the connection pipe 176a, to secure water-tightness between the end portion of the connection pipe 176a and the O ring 192. Accordingly, the passage 163 of the nozzle 142 communicates with the connection pipe 176a through the inside of the O ring 192.

On the other hand, the annular edge portion 168 of the nozzle unit 60 is flush with, or substantially flush with, the distal end surface 104a of the distal end cover 104. In addition, a water-tight (liquid-tight) adhesive is applied between the annular edge portion 168 of the nozzle unit 60 and the distal end surface 104a of the hole portion 138 of the distal end hard portion 72.

When the nozzle unit 60 is detached from the distal end hard portion 72, the nozzle unit 60 can be detached by a work reverse to the work for attaching the nozzle unit 60 to the distal end hard portion 72 described above. Specifically, the flat surface portions 166a and 166b of the head portion 166 in the nozzle unit 60 are held, and the nozzle unit 60 is pulled out of the distal end portion main body 102 and the distal end cover 104.

The present embodiment produces the following effects. The assembly is finished only by inserting the nozzle unit 60 into the hole portion 138 of the distal end hard portion 72, positioning the nozzle unit 60 in the circumferential direction such that the fluid discharge port 164a of the nozzle unit 60 is opposed to the observation window 24a, and thereafter pushing the nozzle unit 60 into the hole portion 138. In this state, the gasket 144 and the O ring 192 are not compressed until the nozzle unit 60 is pushed into the hole portion 138. In addition, even when the nozzle unit 60 is rotated around the central axis C, no load is applied onto the gasket 144 or the O ring 192. In this state, the structure enables communication of a fluid channel formed of the inside of the connection pipe 176a, the inside of the O ring 192, and the passage 163 inside the nozzle 142, with water-tightness.

Accordingly, the present embodiment provides the endoscope 10 that enables easy attachment of the nozzle 142 to the distal end hard portion 72 of the insertion section 12 and prevents load on the nozzle 142, and the endoscope nozzle unit 60 that can be easily attached to the distal end hard portion 72 of the insertion section 12 and prevents load applied thereon.

When the nozzle unit 60 is detached from the distal end hard portion 72, the nozzle unit 60 can be detached by only holding the flat surface portions 166a and 166b of the head portion 166 of the nozzle 142 in the nozzle unit 60, and pulling out the nozzle unit 60. This structure removes the work for taking off the sealing material, and simplifies the work for fitting the new nozzle unit 60 into the hole portion 138 of the distal end hard portion 72. This structure markedly simplifies the work for exchanging the nozzle unit 60, and achieves reduction in time.

When the nozzle unit 60 is fitted into the hole portion 138 of the distal end hard portion 72, the end surface of the connection pipe 176a is pressed with the O ring 192 disposed between the end surface and the annular edge portion 162a of the nozzle 142, and thereby water-tightness between the nozzle 142 and the connection pipe 176a is secured. The gasket 144 enters the receiving space 188 between the inward flange 186 and the projections 184 of the distal end cover 104. The gasket 144 is pressed with the inclined surface 186b of the inward flange 186, and the gasket 144 is maintained in a deformed state by being compressed with the inclined surface 186b, and thereby the deformed state of the O ring 192 is maintained. With the structure, the gasket 144 secures water-tightness on the side of the distal end surface 104a of the distal end cover 104 in the hole portion 138 of the distal end hard portion 72, and water-tightness from the side of the head portion 166 of the nozzle 142. The position of the nozzle 142 in the rotational direction can be determined in the state where the projections 184 of the distal end cover 104 enter and are engaged with the respective cutout portions 155 of the outward flange 154 of the nozzle 142.

In addition, the projection height of the head portion 166 of the nozzle 142 from the distal end surface 104a can be determined with a difference in hardness between the gasket 144 and the O ring 192, and with the downward reaction force of the gasket 144 stronger than the upward reaction force of the O ring 192, and by abutment of the head portion 166 of the nozzle 142 against the inward flange 186 of the distal end cover 104.

The O ring 192 suitably projects to a position close to the central axis C beyond the end surface of the connection pipe 176a of the distal end portion main body 102, and the internal surface of the annular edge portion 162a of the nozzle 142, by deformation caused by pressing by the annular edge portion 162a of the nozzle 142. Because the O ring 192 is coupled by a flexible material, the O ring 192 removes space between the passage 163 inside the nozzle 142 and the connection pipe 176a of the distal end portion main body 102, and the internal circumferential surface of the O ring 192 forms a smooth projecting shape. This structure prevents water from being left between the connection pipe 176a and the passage 163 of the nozzle unit 60 in feeding water, to the utmost. The nozzle unit 60 according to the present embodiment improves the air/water feed property, with the projections 184 and the inward flange 186 formed in the hole portion 138 in the distal end hard portion 72 of the insertion section 12 according to the present embodiment.

The nozzle unit 60 according to the present embodiment requires no fixing screws to fix the nozzle 142 to the distal end portion main body 102, or requires no application of sealant to adhere the fixing screws. No difficult work is required to fix the nozzle unit 60 according to the present embodiment to the distal end portion main body 102. This structure requires no time for drying the sealant, either, and markedly shortens the worktime to attach the nozzle 142 to the distal end hard portion 72.

In addition, although the present embodiment illustrates the case where the O ring 192 is a member separated from the nozzle 142, the O ring 192 may suitably be formed as one unitary piece with the annular edge portion (proximal end opening) 162a of the nozzle 142.

The following is explanation of a modification of the first embodiment, with reference to FIG. 8.

As illustrated in FIG. 8, in the present modification, the inward flange 186 is formed in a ring shape, not an arc shape. Specifically, the inward flange 186 includes a ring-shaped surface 186c, instead of the arc-shaped surface 186a. The projecting surfaces 184b of the projections 184 project toward the central axis C more than the internal circumferential surface 187 of the ring-shaped inward flange 186 does, from the internal circumferential surface 182 of the through hole 128 of the distal end cover 104.

Although not illustrated, as explained in the first embodiment, the inward flange 186 includes the inclined surface 186b that presses the gasket 144 toward the side (upper surface 184a) close to the projections 184, in the state where the gasket 144 gets over the inward flange 186.

Even when the inward flange 186 of the hole portion 138 of the distal end hard portion 72 is formed as in the present modification, the nozzle unit 60 can also be fitted into the hole portion 138 of the distal end hard portion 72, in the same manner as explained in the first embodiment.

The following is explanation of a second embodiment, with reference to FIG. 9 to FIG. 14. The present embodiment is a modification of the first embodiment. The same members as those in the first embodiment, and members having the same functions as those in the first embodiment are denoted by the same respective reference numerals as those in the first embodiment as much as possible, and detailed explanation thereof are omitted.

Figure 9:
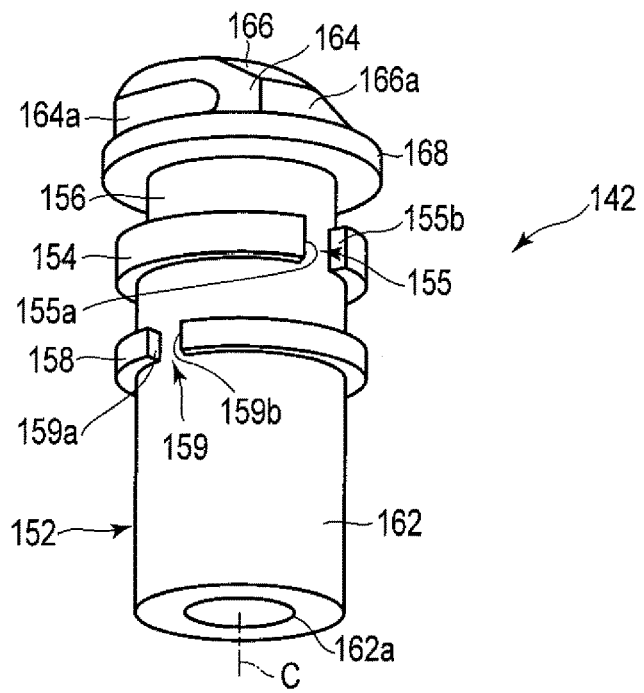
FIG. 9 is a schematic perspective view illustrating a nozzle (cylindrical member) attached to a distal end portion of an insertion section of the endoscope according to the second embodiment.
Figure 10:
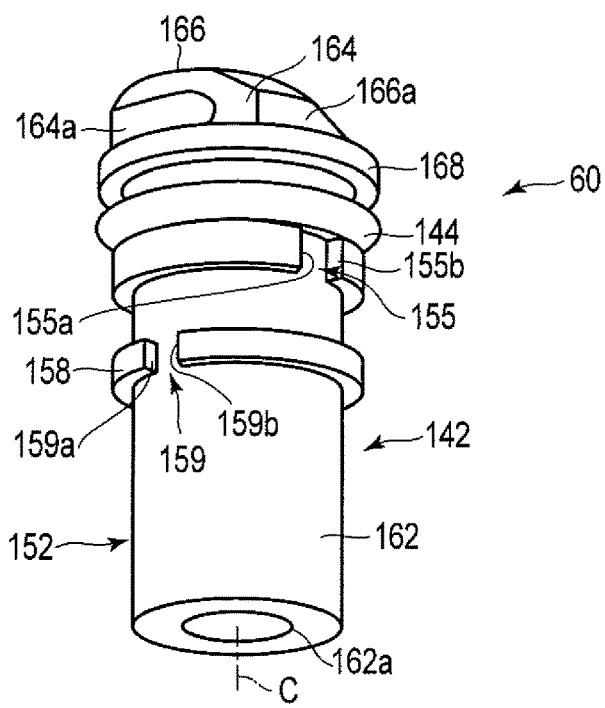
FIG. 10 is a schematic perspective view illustrating a nozzle unit (cylindrical structure) attached to the distal end portion of the insertion section of the endoscope according to the second embodiment.

As illustrated in FIG. 9 and FIG. 10, a second outward flange 158 is formed on the external circumference of the straight duct 162 of the nozzle main body 152 of the nozzle unit 60 according to the present embodiment. Specifically, the nozzle 142 includes the second outward flange 158 on the external circumference of the straight duct 162 of the nozzle main body 152 of the nozzle unit 60. The second outward flange 158 is formed in a position closer to the annular edge portion 162a of the straight duct 162 than the first outward flange 154 is. The second outward flange 158 includes second cutout portions 159 that allow the projections 184 pass along the axial direction of the central axis C. The second cutout portions 159 are shifted in the circumferential direction from the first cutout portions 155 formed in the first outward flange 154. In the present embodiment, the shift amount is set to, for example, 90° with respect to the central axis C, but can be properly set. A space between the edge portion closer to the annular edge portion 162a in the first outward flange 154 and the edge portion more apart from the annular edge portion 162a in the second outward flange 158 is formed slightly larger than the length of the projections 184 along the central axis C. With the structure, the second outward flange 158 enables the projections 184 to be disposed between the second outward flange 158 and the first outward flange 154, by rotation of the nozzle main body 152 around the central axis C.

The following is explanation of the function in the case where the nozzle unit 60 is fitted into the hole portion 138 of the distal end hard portion 72 of the insertion section 12 according to the present embodiment.

The annular gasket 144 is attached to the annular recessed portion 156 of the nozzle 142 illustrated in FIG. 9, to form the nozzle unit 60 (see FIG. 10). The gasket 144 may be disposed in the annular recessed portion 156 from the head portion 166 of the nozzle 142 through the outside of the annular edge portion 168, or may be disposed in the annular recessed portion 156 from the annular edge portion 162a through the outside of the outward flange 154.

As explained in the first embodiment, the O ring 192 is disposed on the annular bottom portion 174 from the distal end surface 104a, through the internal circumferential surface 182 of the through hole 128 of the distal end cover 104, and the internal circumferential surface 172 of the through hole 118 of the distal end portion main body (base member) 102.

Figure 11:
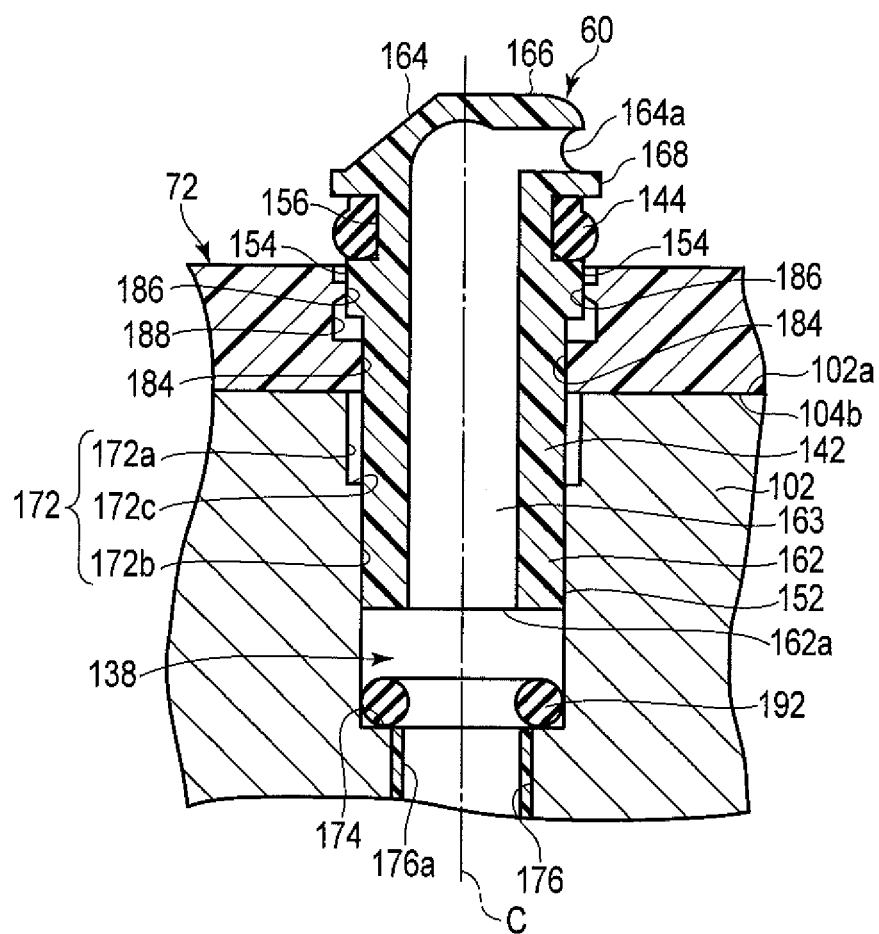
FIG. 11 is a schematic vertical cross-sectional view illustrating a state where a straight duct of the nozzle unit is inserted into a hole portion of a distal end hard portion of the insertion section in the endoscope according to the second embodiment.

As illustrated in FIG. 11, the annular edge portion 162a of the nozzle unit 60 is inserted into the hole portion 138 of the distal end hard portion 72. The second cutout portions 159 of the second outward flange 158 of the nozzle unit 60 are opposed to the projections 184 formed on the internal circumferential surface 182 of the through hole 128 of the distal end cover 104, in the hole portion 138 of the distal end hard portion 72. In this state, the discharge port 164a of the nozzle unit 60 does not face the observation window 24a of the observation optical system 24.

In this state, as illustrated in FIG. 12, the nozzle unit 60 is pushed in toward the depth side of the hole portion 138, and the annular edge portion 162a of the nozzle unit 60 is moved toward the O ring 192 disposed on the annular bottom portion 174 of the hole portion 138. In addition, the projections 184 are caused to pass through the second cutout portions 159 between the end portions 159a and 159b formed in the second outward flange 158. Therefore, the projections 184 abut against the edge portion of the first outward flange 154 closer to the annular edge portion 162a. Specifically, the projections 184 are disposed between the edge portion of the first outward flange 154 closer to the annular edge portion 162a, and the edge portion of the second outward flange 158 more apart from the annular edge portion 162a.

In this state, the gasket 144 is placed on the arc-shaped surface 186a on the upper side (position close to the distal end surface 104a) of the inward flange 186. In this state, the annular edge portion 162a of the straight duct 162 of the nozzle unit 60 is close to the O ring 192 disposed on the annular bottom portion 174 of the hole portion 138.

As illustrated in FIG. 13, the nozzle unit 60 is rotated by 90° around the central axis C, to cause the discharge port 164a of the nozzle unit 60 to face the observation window 24a of the observation optical system 24. Therefore, the orientation of the nozzle unit 60 is regulated with respect to the distal end hard portion 72 of the insertion section 12. In addition, because the projections 184 are disposed in positions distant from the second cutout portions 159 of the second outward flange 158, the nozzle unit 60 is prevented from falling out, even when the nozzle unit 60 is simply pulled from the hole portion 138 in this state.

In this state, the nozzle unit 60 is pushed in toward the depth side of the hole portion 138, and the annular edge portion 162a of the nozzle unit 60 is moved toward the O ring 192 disposed on the annular bottom portion 174 of the hole portion 138. As illustrated in FIG. 14, the gasket 144 is elastically deformed, and moved toward the depth side of the hole portion 138 through the inside of the inward flange 186. On the other hand, the annular edge portion 162a of the straight duct 162 of the nozzle main body 152 pushes the O ring 192 against the annular bottom portion 174. In this state, the projections 184 are caused to pass through the cutout portions 155 between the end portions 155a and 155b formed in the first outward flange 154.

In this state, the O ring 192 is in close contact with the end portion of the connection pipe 176a. In this state, watertightness is secured between the end portion of the connection pipe 176a and the O ring 192. Accordingly, the passage 163 of the nozzle 142 communicates with the connection pipe 176a through the inside of the O ring 192.

When the nozzle unit 60 is detached from the distal end hard portion 72, the nozzle unit 60 can be detached by a work reverse to the work for attaching the nozzle unit 60 to the distal end hard portion 72 described above. Specifically, the flat surface portions 166a and 166b of the head portion 166 in the nozzle unit 60 are held, to cause the projections 184 to abut against the edge portion of the second outward flange 158 apart from the annular edge portion 162a. Thereafter, the nozzle unit 60 is rotated by 90° with respect to the hole portion 138, to cause the projections 184 to pass through the second cutout portions 159, and the nozzle unit 60 is pulled out of the distal end portion main body 102 and the distal end cover 104.

The present embodiment produces the following effects.

Because the second cutout portions 159 are formed in the second outward flange 158, when the nozzle unit 60 is attached to the distal end hard portion 72, the nozzle unit 60 is prevented from falling out of the hole portion 138, by causing the projections 184 to pass through the second cutout portions 159 and rotating the projections 184 by 90°.

Accordingly, the endoscope 10 according to the present invention has the following features.

The hole portion 138 of the distal end portion main body (base member) 102 includes the internal circumferential surface 172. The internal circumferential surface 172 includes the large-diameter portion 172a having a larger diameter and disposed on the side opposed to the rear surface 104b opposite to the distal end surface 104a of the distal end cover 104, and the small-diameter portion 172b having a smaller diameter than that of the side close to the distal end cover 104 and disposed on the side close to the annular bottom portion 174. The nozzle 142 includes the second outward flange 158 that is formed on the external circumferential surface of the straight duct 162 of the nozzle main body 152 and in a position closer to the annular edge portion (proximal end opening) 162a of the straight duct 162 than the first outward flange 154 is. The second outward flange 158 includes the second cutout portions 159 that cause the projections 184 to pass along the axial direction of the central axis C and are disposed in positions shifted from the first cutout portions 155 in the circumferential direction from the central axis C, and enables disposition of the projections 184 between the second outward flange 158 and the first outward flange 154 when the nozzle main body 152 is rotated around the central axis C. The second outward flange 158 is disposed in the large-diameter portion 172a, in the state where the nozzle 142 is fitted into the hole portion 138.

Figure 15:
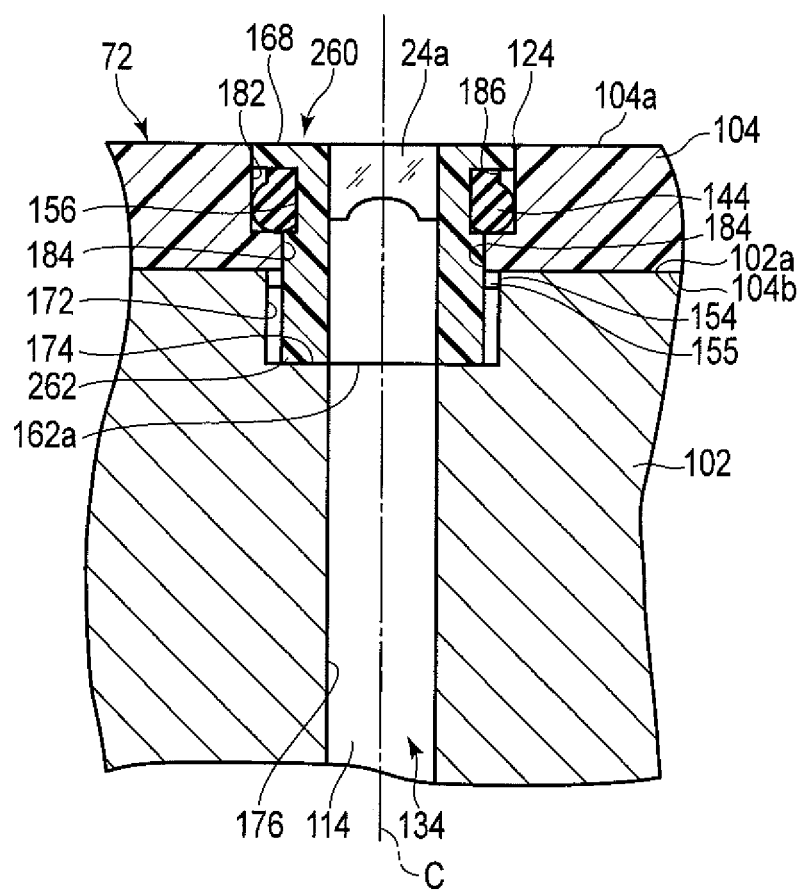
FIG. 15 is a schematic vertical cross-sectional view illustrating a state where a straight duct (cylindrical member) of an objective lens unit (cylindrical structure) is inserted into a hole portion of a distal end hard portion of an insertion section in an endoscope according to a third embodiment, and the objective lens unit is attached to the distal end hard portion.

The following is explanation of a third embodiment, with reference to FIG. 15. The present embodiment is a modification of the first and second embodiments. The same members as those in the first and second embodiments, and members having the same functions as those in the first and second embodiments are denoted by the same respective reference numerals as those in the first and second embodiments as much as possible, and detailed explanation thereof are omitted.

As illustrated in FIG. 15, the present embodiment illustrates an example in which an objective lens unit (endoscope cylindrical structure) 260 that obtains an image of a subject is used, instead of the nozzle unit (cylindrical structure) 60 explained in the first and second embodiments. The objective lens unit 260 is disposed in a hole portion 134. The hole portion 134 is formed of a through hole 114 of the distal end portion main body 102, and the observation optical system through hole (second hole portion) 124 of the distal end cover 104. The through hole 124 of the distal end cover 104 is formed in a shape similar to that of the air/water feed through hole (second hole portion) 128. The through hole 114 of the distal end portion main body 102 includes an internal circumferential hole 172. In this example, the internal circumferential surface 172 is provided with no step portion 172c illustrated in FIG. 5C, but the internal circumferential surface 172 is provided with the annular bottom portion 174.

The objective lens unit 260 according to the present embodiment includes an objective lens holding frame 262 that holds an objective lens (observation window) 24a, and the gasket (first elastic member) 144. The objective lens holding frame 262 is formed of a cylindrical member. The objective lens 24a is fixed at the distal end of the objective lens holding frame 262. The objective lens holding frame 262 includes a holding frame main body (cylindrical member) 152, the outward flange (first outward flange) 154, and the annular recessed portion 156 in which the gasket 144 is disposed. Specifically, the portion of the objective lens holding frame 262 disposed in the hole portion 134 is formed similar to the nozzle 142 of the nozzle unit 60. In the holding frame main body 152, a publicly-known lens unit formed of a combination of a plurality of lenses is provided between the annular edge portion (proximal end opening) 162a and the observation window (distal end opening) 24a. This structure enables imaging of the subject facing the observation window 24a with the imaging unit 24b.

Because the portion of the objective lens holding frame 262 disposed in the hole portion 134 is formed similar to the nozzle 142 of the nozzle unit 60, the objective lens holding frame 262 can also be fixed in the distal end hard portion 72, in the same manner as the nozzle 142 fixed in the distal end hard portion 72 of the insertion section 12. In this case, the through hole 124 of the distal end portion main body 102 requires no O ring 192, unlike the nozzle unit 60 disposed in the through hole 118.

The through hole 114 of the distal end portion main body 102 includes the cylindrical circumferential surface 172 that defines the central axis C, the annular bottom portion 174, and the communicating hole 176. The cylindrical circumferential surface 172, the annular bottom portion 174, and the communicating hole 176 are provided with the imaging unit 24b (see FIG. 2) of the observation optical system 24.

As described above, the cylindrical member is applicable to the nozzle unit 60, the objective lens unit 260, and other illumination units.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
an insertion section having (1) a longitudinal axis, (2) a distal end, (3) an internal circumferential surface that defines a hole with an opening in the distal end and extending from the opening along the longitudinal axis, (4) a first projection projecting inwardly in a radial direction from the internal circumferential surface, and (5) a second projection projecting inwardly in a radial direction from the internal circumferential surface that is (a) spaced from the first projection and (b) located between the first projection and the distal end;
a cylindrical member (1) disposed in the hole, (2) extending along the longitudinal axis, (3) having an external circumferential surface, and (4) having a first outward flange provided on the external circumferential surface that extends outwardly from the external circumferential surface; and
an elastic member provided on the external circumferential surface of the cylindrical member and located between the first projection and the second projection; wherein:
the outward flange has end portions that (1) are opposed to each other in a circumferential direction of the longitudinal axis and (2) define a first cutout;
the first projection is disposed in the first cutout; and
the elastic member (1) is elastically deformable and configured to slide over the second projection when the cylindrical member is inserted into the hole of the insertion section and (2) interacts with the second projection to urge the cylindrical member away from the distal end of the insertion section.

2. The endoscope according to claim 1, wherein:
the cylindrical member has a bottom portion; and
the endoscope further comprises another elastic member (1) located in the hole, (2) abutting against the bottom portion and (3) elastically deformed when the cylindrical member is disposed in the hole such that the another elastic member urges the cylindrical member toward the opening.

3. The endoscope according to claim 2, wherein the elastic member is less easily deformable than the another elastic member.

4. The endoscope according to claim 1, wherein the second projection includes an inclined surface which (1) is formed in an arc or ring shape, (2) is inclined with respect to the longitudinal axis from the internal circumferential surface towards the opening, and (3) interacts with the elastic member.

5. The endoscope according to claim 1, further comprising:
a regulating portion (1) provided on the external circumferential surface of the cylindrical member and (2) having a shape that will not fit into the opening of the hole.

6. The endoscope according to claim 1, wherein:
the cylindrical member has a bottom portion;
the endoscope further comprises a second outward flange (1) provided on the external circumferential surface of the cylindrical member, (2) located between the first outward flange and the bottom portion and (3) defining a second cutout shifted in the circumferential direction from the first cutout; and
when the cylindrical member is inserted into the hole, the first projection passes through the second cutout.

7. The endoscope according to claim 1, wherein the insertion section includes:
a base member that forms a part of the hole and receives the cylindrical member; and
a cover member (1) that forms a part of the hole, including the opening of the hole, and (2) includes the first projection and the second projection.

8. The endoscope according to claim 7, wherein:
the base member defines a first portion of the internal circumferential surface, the first portion including (1) a small-diameter portion having a first diameter and formed on a side of the internal circumferential surface and (2)

a large diameter portion having a second diameter and formed on a side of the internal circumferential surface;

the large diameter portion is between the small-diameter portion and the cover member;

the second diameter is larger than the first diameter; and the second outward flange is disposed in the large diameter portion.

9. The endoscope according to claim 1, wherein:

the second projection includes circumferentially opposed end portions, and the first projection is disposed between the end portions when viewed from the opening.

10. The endoscope according to claim 1, wherein:

the insertion section includes an observation window; and the cylindrical member is a nozzle unit including a fluid channel to feed fluid to the observation window.

11. The endoscope according to claim 1, wherein the cylindrical member is a lens unit.

12. The endoscope according to claim 1, wherein the first projection is configured to engage the first cutout.

\* \* \* \* \*